US012805972B2

(12) United States Patent
Matsui

(10) Patent No.: US 12,805,972 B2
(45) Date of Patent: Nov. 24, 2026

(54) IDENTIFICATION OF A PERSON BY THE UNIQUE CHEMICAL COMPOSITION OF A BIOMATERIAL IN DIFFERENT PHASES

(71) Applicant: CareTech Human Inc., Lewes, DE (US)

(72) Inventor: Denys Vladymyrovych Matsui, Lewes, DE (US)

(73) Assignee: CareTech Human Inc., Lewes, DE (US)

( * ) Notice: Subject to any disclaimer, the term of this patent is extended or adjusted under 35 U.S.C. 154(b) by 281 days.

(21) Appl. No.: 18/538,877

(22) Filed: Dec. 13, 2023

(65) Prior Publication Data

US 2024/0115350 A1 Apr. 11, 2024

Related U.S. Application Data

(63) Continuation of application No. PCT/US2022/033838, filed on Jun. 16, 2022.

(Continued)

(51) Int. Cl.
*A61B 5/00* (2006.01)
*A61B 5/097* (2006.01)
(Continued)

(52) U.S. Cl.
CPC .............. *A61B 90/90* (2016.02); *A61B 5/097* (2013.01); *A61B 10/0038* (2013.01);
(Continued)

(58) Field of Classification Search
CPC ..... A61B 90/90; A61B 5/097; A61B 10/0038; A61B 10/0045; A61B 2010/0087;
(Continued)

(56) References Cited

U.S. PATENT DOCUMENTS 4,884,435 A 12/1989 Ehara
6,401,538 B1 6/2002 Han et al.
(Continued)

FOREIGN PATENT DOCUMENTS

CN 113711210 A * 11/2021 ............. G06V 40/60
DE 102008041861 A1 * 3/2010 ............. G06F 21/32
(Continued)

OTHER PUBLICATIONS

International Search Report and Written Opinion for International Application No. PCT/US2022/33838, dated Oct. 26, 2022.
(Continued)

*Primary Examiner* — May A Abouelela
(74) *Attorney, Agent, or Firm* — Foley Hoag LLP; Erik A. Huestis; Vincenzo DiMonaco

(57) ABSTRACT

A system for automated identification of a person by the unique chemical composition of a biomaterial includes a biomaterial sample intake port in fluid communication with a sampling reservoir. The system includes a proximity sensor configured to detect the presence of a person at the biomaterial sample intake port and to produce a signal indicative thereof. The system includes at least one sensor in fluid communication with the sampling reservoir and configured to receive the signal from the proximity sensor and in response, determine a timeframe to analyze the biomaterial sample and extract at least one datum from the biomaterial sample during the timeframe. The system includes a computing node configured to receive the at least one datum from the sensor, extract a first feature from the at last one datum, compare the first feature to a stored feature associated with the person, thereby identifying the person.

14 Claims, 9 Drawing Sheets

Related U.S. Application Data

(60) Provisional application No. 63/211,801, filed on Jun. 17, 2021.

(51) Int. Cl.
*A61B 10/00* (2006.01)
*A61B 90/90* (2016.01)
*G16H 10/60* (2018.01)

(52) U.S. Cl.
CPC ......... *A61B 10/0045* (2013.01); *G16H 10/60* (2018.01); *A61B 2010/0087* (2013.01)

(58) Field of Classification Search
CPC ..... A61B 5/082; A61B 5/1171; A61B 5/1468; A61B 5/1491; A61B 5/207; A61B 5/6898; A61B 2505/07; A61B 2562/0219; A61B 2562/0257; A61B 5/14517; A61B 5/6891; G16H 10/60; G06F 21/32
See application file for complete search history.

(56) References Cited

U.S. PATENT DOCUMENTS

| | | | | |
|---|---|---|---|---|
| 9,848,075 | B1 * | 12/2017 | Ahmad | G16H 40/67 |
| 10,839,528 | B2 * | 11/2020 | Ross | G06F 21/32 |
| 11,034,331 | B1 * | 6/2021 | Min | B60R 25/252 |
| 11,556,625 | B2 * | 1/2023 | McNulty | G06F 21/32 |
| 11,610,204 | B1 * | 3/2023 | Osterkamp | G07C 9/37 |
| 11,766,213 | B1 * | 9/2023 | Kahn | A61B 5/4818<br>600/529 |
| 2003/0192112 | A1 | 10/2003 | Ware | |
| 2006/0206725 | A1 * | 9/2006 | Milgramm | G07C 9/37<br>713/186 |
| 2014/0096590 | A1 | 4/2014 | Amin et al. | |
| 2014/0302893 | A1 | 10/2014 | Dhavaloganathan | |
| 2015/0123766 | A1 | 5/2015 | St. John | |
| 2015/0330958 | A1 | 11/2015 | Carney et al. | |
| 2016/0106935 | A1 | 4/2016 | Sezan et al. | |
| 2017/0089875 | A1 | 3/2017 | Hasegawa et al. | |
| 2019/0289001 | A1 * | 9/2019 | Milgramm | G06F 21/6236 |
| 2020/0265133 | A1 * | 8/2020 | Mokhasi | G06Q 20/4012 |
| 2021/0021421 | A1 * | 1/2021 | Rosenkrantz | G06F 21/32 |
| 2022/0354383 | A1 * | 11/2022 | Jia | A61B 5/087 |
| 2022/0382839 | A1 * | 12/2022 | Vargas | G06N 3/0464 |
| 2024/0005432 | A1 * | 1/2024 | Aman | G16H 50/80 |

FOREIGN PATENT DOCUMENTS

| | | | | |
|---|---|---|---|---|
| IT | 202000013279 | A1 * | 12/2021 | G06V 20/52 |
| WO | WO-00/78204 | A2 | 12/2000 | |
| WO | WO-2022/266353 | A1 | 12/2022 | |
| WO | WO-2022/266353 | A9 | 2/2023 | |

OTHER PUBLICATIONS

Shu, et al. "Identification authentication scheme using human body odour." 2014 IEEE International Conference on Control Science and Systems Engineering. IEEE, Dec. 29, 2014.

Wongchoosuk, et al. "Detection and classification of human body odor using an electronic nose." Sensors 9.9 (Sep. 9, 2009): 7234-7249.

Yang, et al. "Human body odor based authentication using machine learning." 2018 IEEE Symposium Series on Computational Intelligence (SSCI). IEEE, Nov. 18, 2018.

Supplementary European Search Report for EP Application No. 22825840.6 dated Mar. 21, 2025.

* cited by examiner

910

IDENTIFICATION OF A PERSON BY THE UNIQUE CHEMICAL COMPOSITION OF A BIOMATERIAL IN DIFFERENT PHASES

CROSS-REFERENCE TO RELATED APPLICATIONS

This application is a Bypass Continuation of International Application No. PCT/US22/33838, filed on Jun. 16, 2022, which claims the benefit of U.S. Provisional App. No. 63/211,801, filed on Jun. 17, 2021. Each of these prior applications are hereby incorporated by reference in their entirety.

BACKGROUND

The modern world is characterized by numerous trends in the healthcare sector. The percentage of the aged population is on the rise in many countries. At the same time, the number of diseases is growing, including, but not limited to cardiovascular, infectious, gastroenterological as well as endocrine diseases, urology diseases including but not limited to urinary tract infections (UTI), benign prostatic hyperplasia (BPH), overactive bladder, immune-mediated rheumatic diseases, including arthritis, inflammatory diseases of the spine, connective tissue diseases and vasculitis, bacterial infections, for early detection of which the possibility of using different methods of medical diagnostics is being studied. Blood tests are the gold standard for diagnostics, although diagnostic methods based on sweat, saliva, exhaled air as well as urine and feces have been gaining popularity in recent years. It is known that the listed diseases lead to the appearance of either characteristic biomarkers or metabolic changes in general. Thus, the types of biomaterials listed above, such as urine, feces, sweat, saliva, and exhaled air, allow measurements to be carried out non-invasively, regularly, even at home. In addition, they are often much more affordable.

The operating principle of such diagnostic methods is based on the control of metabolic changes in general or on the appearance of certain chemical biomarkers (or their combinations). In particular, the analysis of volatile organic compounds that may be contained in urine, feces, sweat, saliva, and exhaled air, has become widespread. Many of them have already received the status of biomarkers and are actively used in the diagnosis of diseases.

From the perspective of the diagnostic devices themselves, a smart toilet or toilet-integrable systems may be provided that turns the natural voiding process into constant collection of vital health information. Having created such a solution, early diagnosis and control of diseases can organically fit into a person's habitual procedures and will not require any additional actions and time/efforts.

Embodiments of the present disclosure relate to person identification, and more specifically, to identifying individual people based on the chemical composition of biomaterial associated with that person. Embodiments of the present disclosure may operate in environments that may be optimized by personalized medical treatment, disease screening, health screening, clinical diagnostics, and/or personalized health status analysis such as wellness diagnostics.

BRIEF SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system for automated identification of a person by the unique chemical composition of a biomaterial includes a biomaterial sample intake port in fluid communication with a sampling reservoir. The system includes a proximity sensor configured to detect the presence of a person at said biomaterial sample intake port and to produce a signal indicative thereof. The system includes at least one sensor in fluid communication with said sampling reservoir and configured to receive said signal from said proximity sensor and in response, determine a timeframe to analyze said biomaterial sample and extract at least one datum from said biomaterial sample during said timeframe. Said system includes a computing node that is configured to receive said at least one datum from said sensor, extract a first feature from said at last one datum, compare said first feature to a stored feature associated with said person, thereby identifying said person.

To achieve these and other advantages and in accordance with the purpose of the disclosed subject matter, as embodied and broadly described, the disclosed subject matter includes a method for automated identification of a person by the unique chemical composition of a biomaterial. Said method includes receiving a biomaterial sample at a biomaterial sample intake port in fluid communication with a sampling reservoir. Said method includes extracting at least one datum from said biomaterial sample via at least one sensor disposed in said sampling reservoir. Said method includes extracting a first feature from said at least one datum. Said method includes comparing said first feature to a stored feature, wherein said stored feature is retrieved from at least one database. Said method includes identifying said person.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE SEVERAL VIEWS OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION

Reference will now be made in detail to exemplary embodiments of the disclosed subject matter, an example of which is illustrated in the accompanying drawings. The method and corresponding steps of the disclosed subject matter will be described in conjunction with the detailed description of the system.

For the purposes of this disclosure, person identification may include person re-identification (ReId). For the purpose of this disclosure, "person re-identification" is the task of associating new data belonging to a person with previous information collected, stored, and retrieved from the that person. The described embodiments are aimed at creating the possibility of complete automation of all types of medical diagnostic systems. With embodiments of the invention, the identification of a person can be performed automatically with high accuracy. Identification is performed by comparing the characteristics of a taken biomaterial sample with the data set of an individual subject available in one or more system databases. Biomaterial samples include but are not limited to urine, feces, exhaled air, saliva, sweat, and their gas phases.

Automatic identification of a person by the unique chemical composition of a biomaterial, like urine odor (VOCs concentration and/or chemical structure), and automatically comparing it with the information in the database and resulting association of a new sample with the concrete user in some embodiments, may be used as a part of fully automated medical screening or/and a diagnostic system. Such a system would benefit from the identification function when it is combined with one or more (but not limited to) of the following: automated detection of the subject in the testing place, manual initiation system, an automated system to detect the right sampling moment, automated sampling system, information extraction system, a system that will evaluate health conditions and a system that can present results to a user or share it with other medical information systems.

Figure 1:
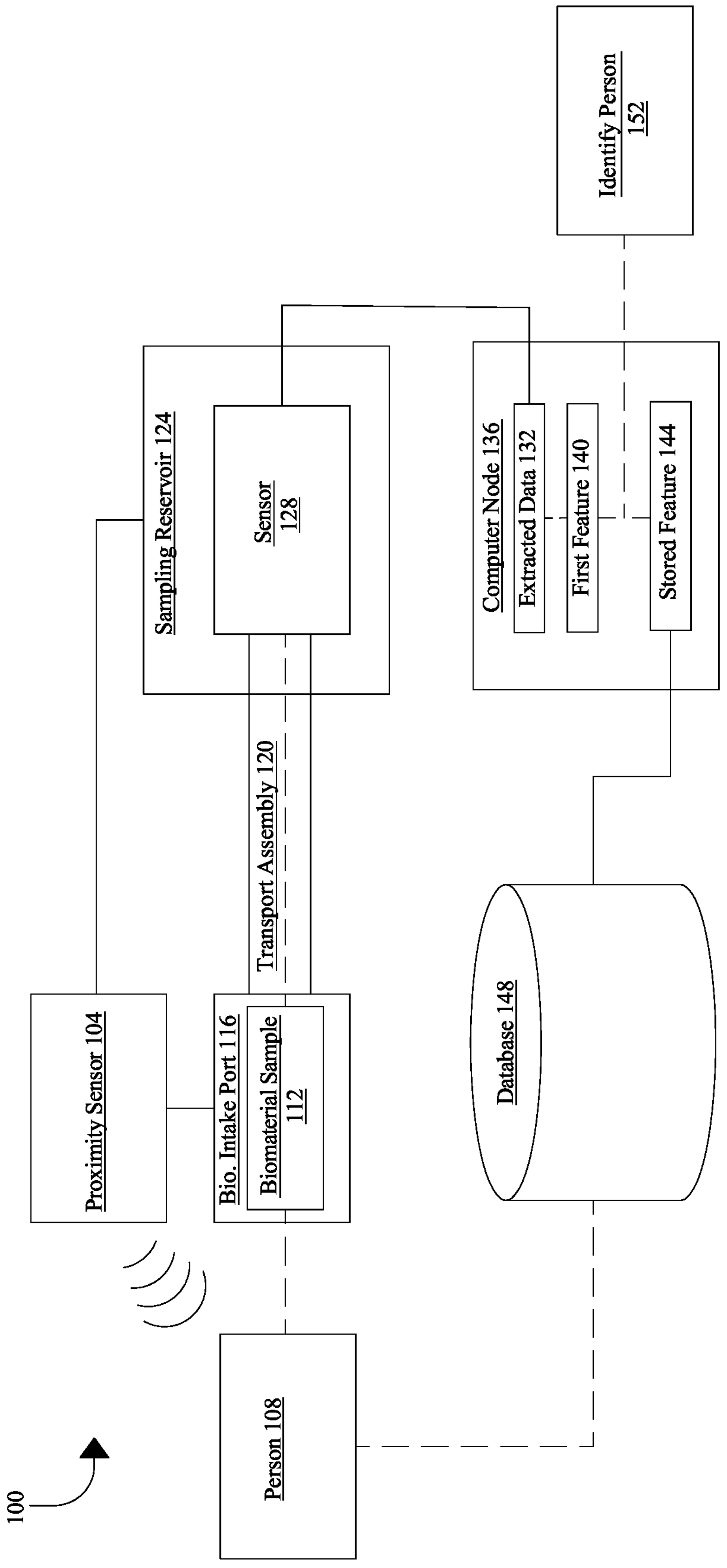
FIG. 1 is a schematic diagram of a system for identification of a person by the chemical composition of a biomaterial sample according to embodiments of the present disclosure.

The methods and systems presented herein may be used for identification of a person by a biomaterial sample analysis. The disclosed subject matter is particularly suited for analysis of extracted data of a biomaterial sample associated with a person and matching said extracted data with stored data associated with the person, thereby identifying the person by the biomaterial sample. For the purposes of explanation and illustration, and not limitation, an exemplary embodiment of the system in accordance with the disclosed subject matter is shown in FIG. 1 and is designated generally by reference character 100. Similar reference numerals (differentiated by the leading numeral) may be provided among the various views and Figures presented herein to denote functionally corresponding, but not necessarily identical structures.

Person identification includes a plurality of steps and methodologies in varying order and implementations. One embodiment thereof can include delivering one or more biomaterial samples to one or more sensors, extracting data from the biomaterial sample based on the measurements of the one or more sensors, pre-processing the extracted data to extract meaningful features, and then matching the biomaterial based on the extracted meaningful features to data and/or features retrieved from a database of a pre-identified person.

The device modules, solutions and subsystems can be assembled in one device or stand-alone solutions or they can operate together being physically divided. The operation of hardware subsystems can be designed using any one or more microcontrollers, and in some embodiments, using ESP32, ESP32-S and ESP32-C. The device modules, solutions, and subsystems can be powered by a battery or by a rechargeable accumulator or be connected to the power supply. The device modules, solutions and subsystems can be assembled in any form-factor and additionally have specific mounting devices to clip to a toilet bowl or any other place in which the described system is deployed.

The device can be additionally equipped with buttons, LEDs, beepers, monitors, speakers, and sensing panels. Mentioned elements can form antidotal product subsystems aimed to provide additional functions for users such as, but not limited to, data and results presentation, operation, on/off/reset functions, process steps indications, errors indications, and manual person identification. This subsystem can be integrated with other product subsystems or form a stand-alone module for users' convenience. In particular, in the case of a urine analyzer, it might be prudent to place this product module on the wall near a toilet bowl so the user will not have to stop in order to operate the device (e.g., push buttons, read the information on the monitor panel).

The device and all other solution subsystems can be a part of a bigger solution or infrastructure. In particular the solution may include systems or methods that push results to other IT systems, medical information systems, Internet of Things (IoT) devices, smartphones or be controlled in another manner.

Now referring to FIG. 1, a system 100 for identification of a person by the chemical composition of a biomaterial sample is presented in flow diagram form. Embodiments of system 100 can be used for any relevant product application such as breath analyzers, saliva analyzers, in-toilet waste analyzers, and/or seat analyzing patches. Embodiments of the present disclosure can be designed for in-home use of an individual, commercial use in businesses, smart houses, smart buildings, hospitals, public point-of-care settings, and the like. Embodiments of the present disclosure can be designed for a plurality of biomaterial samples such as urine, feces, sweat, saliva, and/or exhaled air, among others. Embodiments of the present disclosure can utilize Metal-Oxide semiconductor-based MEMS sensors to measure one or more parameters of urine samples.

Embodiments of system 100 can be a software and hardware complex for automatic identification of a person by the unique chemical composition of a biomaterial, predominantly utilizing biomaterial samples such as urine, feces, sweat, saliva, and exhaled air. Moreover, the claimed system and method are adapted for the identification of a person based on biomaterials of the mentioned types in various states of aggregation (phases), in particular in solid, liquid, or gaseous phases or a combination thereof. Such a software and hardware complex and its one or more algorithms allow automating the processes of personalized medicine, e.g., determining the quality of drug metabolization, medical diagnostics, in particular, clinical diagnostics, and diagnostics of a person's health status (wellness diagnostics).

With continued reference to FIG. 1, system 100 includes proximity sensor 104. Proximity sensor 104 may include one or more sensors working in tandem or individually. Proximity sensor 104 may be disposed in or on a portion of system 100 such as the bowl of a toilet, on a wall of a bathroom, a door or corridor, embedded in the ceiling of a room, or the like. Proximity sensor 104 is configured to detect the presence of a person 108. Proximity sensor 104 may utilize one or more technologies and methodologies to detect person 108. For example, proximity sensor 104 may be a motion sensor, sound sensor, vibration sensor, SONAR, time-of-flight sensor, various light sensors, or the like. For the purposes of this disclosure, "proximity sensor" is one or more components configured to detect a person has entered an area associated with the production of a biomaterial sample. For example and without limitation, proximity sensor 104 may include an infrared sensor that detects the warmth of a person's body as they enter a space where system 100 is disposed.

Proximity sensor 104 may include a manual switch such as a button disposed on or near the rest of system 100. Proximity sensor 104 is configured to trigger one or more other components of system 100 as described below. For example, person 108 may be preparing to use the restroom to submit a biomaterial sample in the form of urine. Person 108 may then press the button, activate the switch, actuate a lever, pull a string, or other manual interface that connects one or more circuits, relays, or the like to activate another component of system 100. Proximity sensor 104 may be one or more smartphone applications loaded onto person 108 smartphone that tracks location utilizing GPS technology that in turn triggers one or more components when person 108 is within a predetermined distance from proximity sensor 104. Proximity sensor 104 may be one or more of the above described technologies used in concert or sequentially. Proximity sensor 104 may be a pyroelectric infrared (PIR) motion sensor. The PIR sensor may be disposed in a restroom where system 100 is located. PIR sensor may be adjustable to trigger at differing distances. For example, and without limitation, the PIR sensor may be configured to generate electrical signals to activate one or more other electrical components of system 100 when person 108 reaches 20 centimeters (cm) to 2 meters (m) from the PIR sensor.

Proximity sensor 104 may be configured to generate one or more signals in response to detection of person 108. For example and without limitation, proximity sensor 104 may be configured to generate an electrical signal and convey said signal to another sensor such as the sensor 128 (described below). Proximity sensor 104 may be electrically coupled to one or more computing devices, processors, controllers, or other electronic devices as described herein. Proximity sensor 104 may be electrically coupled to one or more remotely located servers and/or cloud technologies such as those described below. According to embodiments of the disclosed subject matter, any of the described elements may produce electrical, optical, radio, or other types of signals to communicate with another one or more components of system 100.

With continued reference to FIG. 1, system 100 may be used by person 108. Person 108 may be a client, patient, or walk-in of a medical provider. Person 108 may be someone seeking medical attention in an appointment or emergency scenario. Person 108 may be a transfer patient from one or more alternate medical provider services. Person 108 must be associated with one or more elements of data such as stored feature 144 (below) stored in database 148 (below) electrically or otherwise coupled to system 100. Person 108 may have stored feature 144 that has been processed, categorized and organized according to one or more methodologies of system 100 and database 148. Person 108 may be associated with a stored feature 144 configured to be retrieved by embodiments of the present disclosure and further process, match, or otherwise manipulated by one or more elements of system 100.

With continued reference to FIG. 1, system 100 for identification of a person by a chemical composition of a biomaterial sample includes the biomaterial sample 112. For the purpose of this disclosure, "biomaterial sample(s)" is one or more bodily-produced material including one or more indicative characteristics associated with the person whom produced it. The chemical composition of urine, feces, exhaled air, saliva and sweat is a consequence of unique and personal metabolic processes. These metabolic processes are determined by the type and amount of foods and/or liquids consumed, living conditions, the specific features of the nervous system, and other external factors, i.e., unique and lead to the formation of a unique set of chemical elements in human excreta, which can be called "a subject's metabolic fingerprint". Having a sufficiently accurate system for identifying these chemical elements and their concentration, it is possible to build an identification system based on such a metabolic fingerprint, the data about which can be obtained and stored by embodiments of system 100.

For example, a biomaterial sample can be, urine, which contains volatile organic compounds (VOC) which are organic chemicals that have a high vapor pressure at room temperature. In other words, they can be turned into a gas without any additional action. Therefore the biomaterial sample may be a liquid and the gases it produces or changes phases into. Examples are ammonia, acetone, nitrogen oxides, and/or some aldehydes, etc. VOCs occur in human specimens, in particular urine, due to metabolization process, physical activity, diet, and/or diseases, among others. For example and without limitation, more than 500 VOCs can be present in human urine. The VOC concentration and combination are unique or at least, markedly different for each person because of personal metabolic processes, among other factors.

With continued reference to FIG. 1, biomaterial sample 112 may be collected at biomaterial sample intake port 116 in liquid form, such as urine. Biomaterial sample 112 may be evaporated partially or wholly to form biomaterial sample 112 in gaseous form. Biomaterial sample 112 may be evaporated by the one or more physical phenomenon such as vapor pressure or VOCs. Biomaterial sample 112 in liquid form may be partially or wholly evaporated by a heating element. Biomaterial sample 112 may be evaporated for more effective sensing in the case of less volatile chemicals, for example, chemicals that do not evaporate at room temperature and pressure. For example and without limitation, biomaterial sample 112 may be collected, deposited or otherwise taken into the system 100 in a gaseous state. Biomaterial sample 112 in solid form may be sublimated into gaseous form or melted/broken down into liquid form by a heating element. For example and without limitation, person 108 may urinate into a toilet bowl that acts as biomaterial sample intake port 116. There may be a heating element there disposed that evaporates a portion of the urine into gaseous form. The gaseous form of biomaterial sample 112 may be captured by a downstream element of system 100 such as transport assembly 120 (below) and/or sampling reservoir 124 (below) to be analyzed. In particular, a gaseous sample can be taken from a surface gas layer above the liquid and contain volatile chemicals. Evaporation can take place at room temperature or through artificial heating in the reservoir using any known heater, including an optical (laser) or resistance-based heating element or any other technical solutions. The heating element may reach a temperature range of about 150-550 degrees Celsius. The heating element may be integral to sensor 128, coupled thereto, or a standalone element of system 100 communicatively coupled thereto, according to embodiments.

With continued reference to FIG. 1, system 100 for identification of a person by chemical composition of a biomaterial sample may include a transport assembly 120. Transport assembly 120 is configured to transport biomaterial sample 112 to sampling reservoir 124, among other destinations. Transport assembly 120 may be in fluid communication with one or more components of system 100, such as biomaterial sample intake port 116 and/or sampling reservoir 124. Transport assembly 120 may be configured to transport one or more biomaterial samples 112 to one or more destinations in a plurality of phases simultaneously or separately, according to embodiments.

Figure 4:
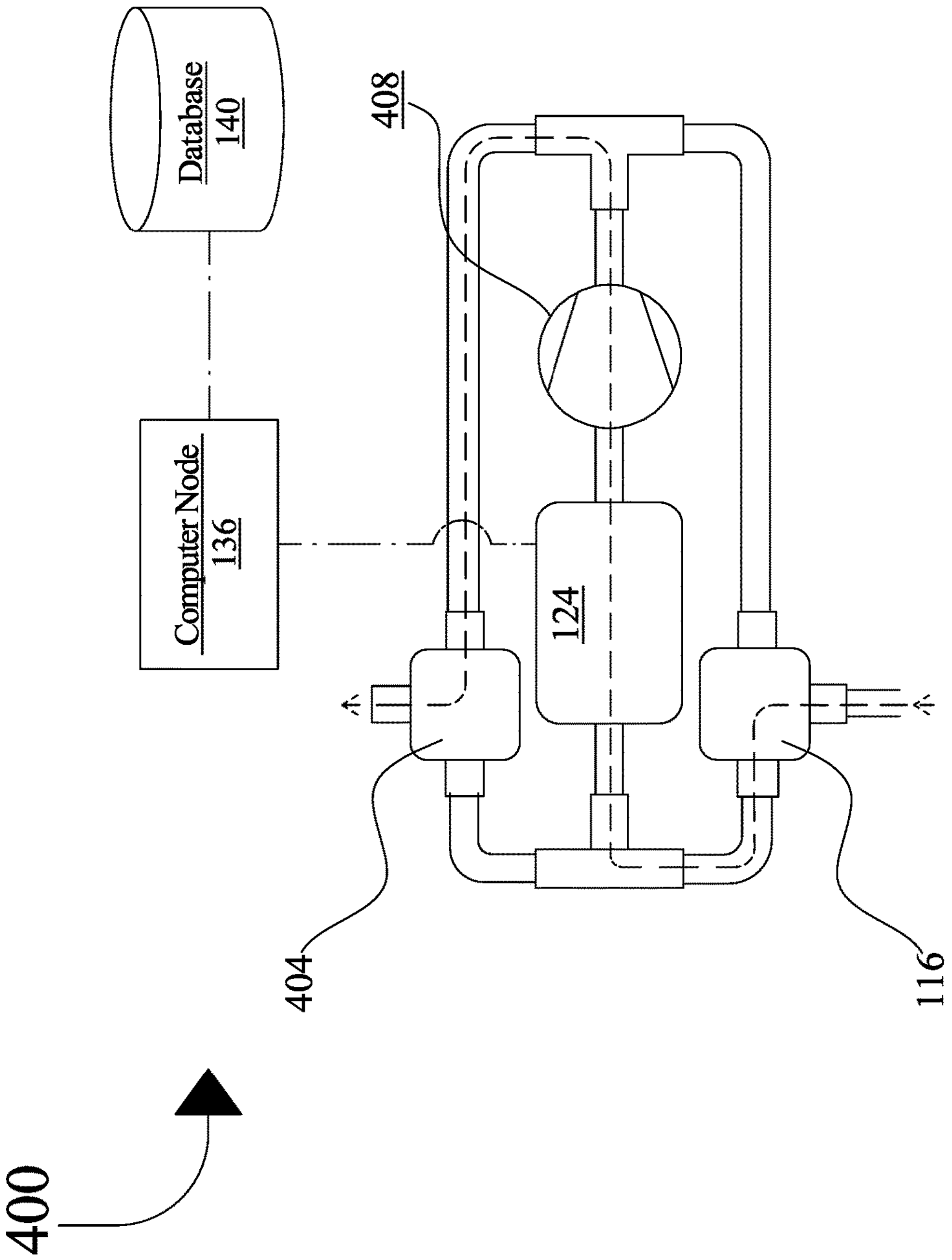
FIG. 4 is a schematic diagram of a transport assembly of a biomaterial sample according to embodiments of the present disclosure.

Referring to FIG. 4, transport assembly 120 may be the same or similar to transport assembly 400, that may include a pump 408 configured to move fluids from high pressure to low pressure. According to embodiments of the disclosed subject matter, pump 408 may be configured to operate with liquid and/or gas (including air). Pump 408 may be located downstream of sampling reservoir 124 or another location, according to embodiments. Transport assembly 400 may include exhaust valve 404. Exhaust valve 404 may be configured to expel biomaterial sample 112 after analysis and processing. Exhaust valve 404 may be configured for use with a plurality of biomaterial samples 112 such as air, gas, liquids, or solids. Transport assembly 120 and/or 400 can be built using said pump, a rarefied air system, or any other equivalent technical solution that provides directional movement of a biomaterial sample 112 (in fluid or solid form) in the system and can be equipped with pumps, valves, transportation mainline and made in the form of a pipe, channel, reservoir or similar structural element. In addition, the sampling system can be equipped with a reservoir for a sample of biomaterial, which is connected to a sample retraction device. A sample retraction device may be configured to extend to collect a sample and retract when sample is collected for analysis, according to embodiments. In some cases, a toilet bowl of a sanitary device itself can be such a reservoir. Transport assembly 120 can be built using an air pump (e.g., 6V Air Pump DC Small Mini 370 Motor Micro Air Pump Oxygen Pump Aquarium 450 mmHG), two 3-way valves, pipes, connectors, and a gas chamber, according to embodiments. The control software (embedded or/and cloud-based) can operate the plurality of valves to open or close and prime and activate the pump to intake sample into the sampling reservoir 124 for further analysis. The biomaterial sampling and transport assembly can operate with any amount of gas. The transport assembly 120 can be connected to the atmosphere and by switching the direction of the airflow the system can be cleaned with ambient air. The system additionally can be supplied with humidity, temperature, and pressure sensors (e.g. Adafruit BME280 I2C or SPI Temperature Humidity Pressure Sensor) for instance, but not limited, to control accidental water intake or overly wet gaseous samples. One of ordinary skill in the art would appreciate that these are only exemplary embodiments of transport assemblies and does not limit the configuration and/or elements found therein.

In embodiments there may be a plurality of sampling reservoirs 124, pumps, valves, connectors, and other elements aimed to make the sampling and sample analysis more efficient or meet product application requirements e.g., simultaneous intake of biomaterial sample 112 from one or more person 108, such as an embodiment integrated into a smart building.

With continued reference to FIG. 1, system 100 for identification of a person by the chemical composition of a biomaterial sample includes at least one sensor 128. Sensor 128 may include a plurality of sensors working in tandem to measure one or more parameters of biomaterial sample 112. Sensor 128 is disposed in, on, or near to biomaterial sample intake port 116 and/or sampling reservoir 124. For example and without limitation, sensor 128 may be disposed on the inside surface of a toilet bowl, on the interior of a tube for person 108 to blow into, adjacent to a toilet seat, or another sampling reservoir configured to analyze biomaterial sample 112. For example and without limitation, sensor 128, which may be one or more MOS sensors may be disposed in sampling reservoir 124 configured for the sampling of a gas, such as that shown in FIG. 6. Sampling reservoir 124 may include a gas chamber, transportation tube (such as any of transport assembly), device box, the interior of an entire room, the interior of a private or public motor vehicle, or the like.

Figure 2:
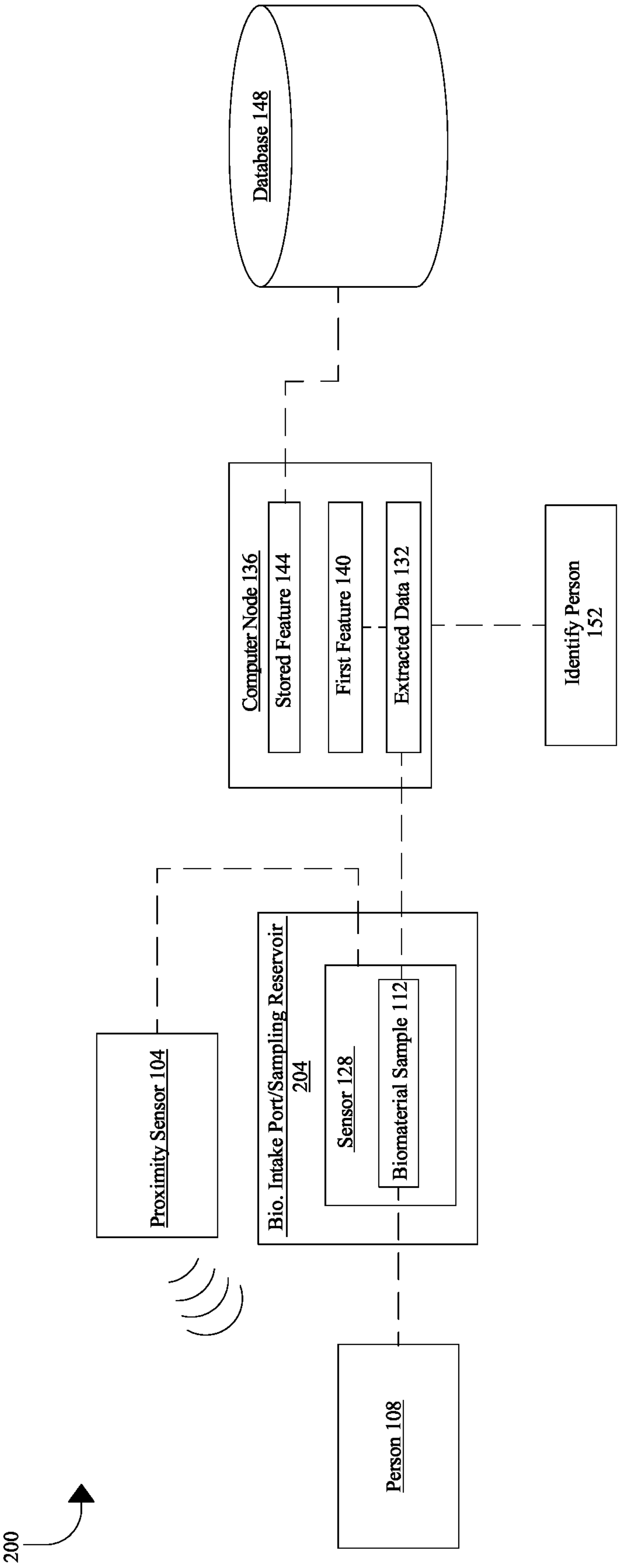
FIG. 2 is a schematic diagram of a system for identification of a person by the chemical composition of a biomaterial sample according to embodiments of the present disclosure.
Figure 7:
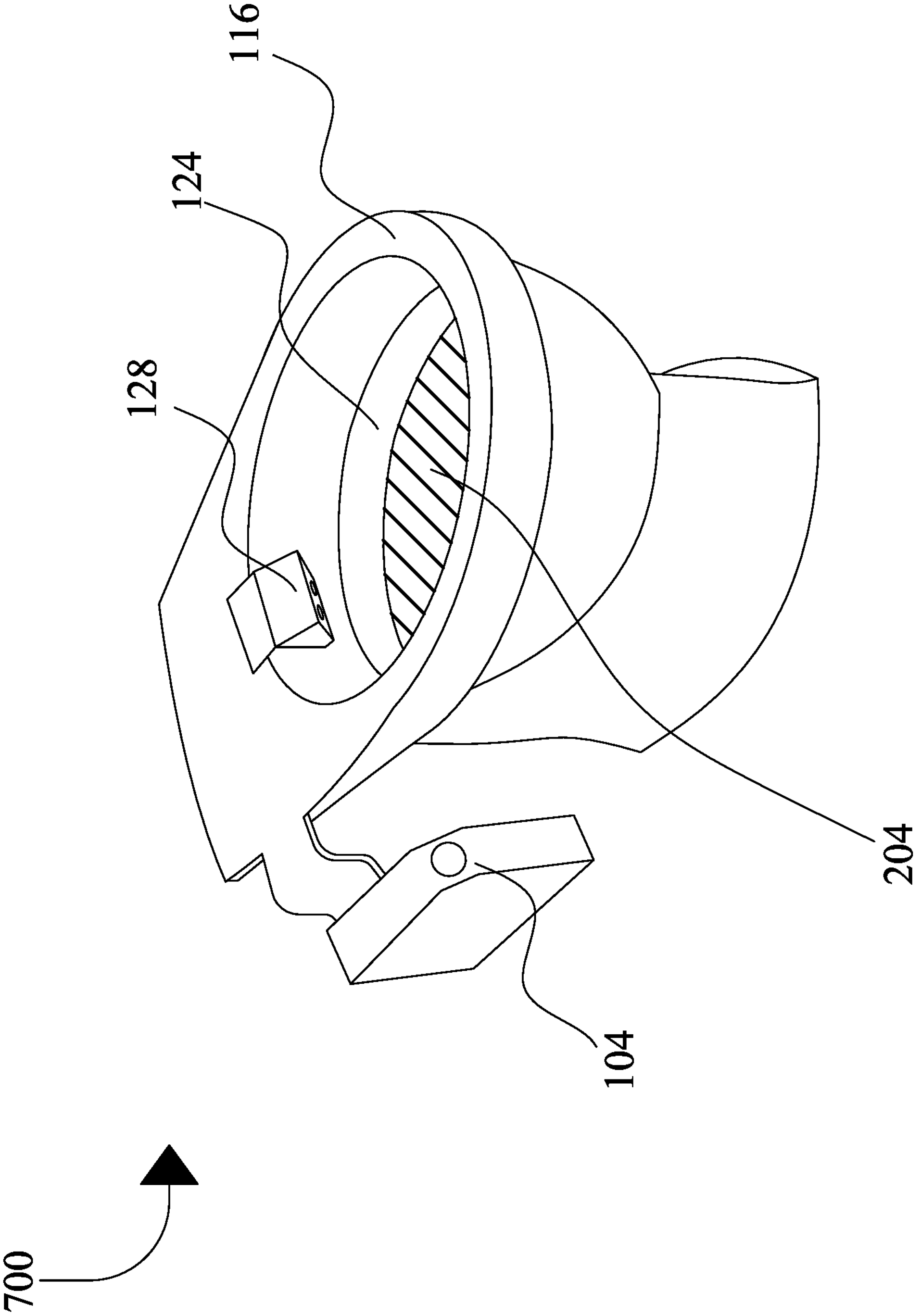
FIG. 7 is a perspective view of a biomaterial sample intake port and sampling reservoir used in a sanitation device according to embodiments of the present disclosure.

Referring now to FIG. 2, system 200 for identification of a person by chemical composition of biomaterial sample includes a biomaterial sample intake port and sampling reservoir 204. Biomaterial sample intake port and sampling reservoir 204 may be the same receptacle or different portions of the same body. For example and without limitation, biomaterial sample intake port 116 and sampling reservoir 204 may be a toilet bowl. That is to say that person 108 deposits their biomaterial sample 112 into the toilet bowl and the analysis of biomaterial sample 112 is performed within said toilet bowl. The arrangement of the biomaterial sample intake port and sampling reservoir does not preclude methodologies described herein such as heating biomaterial sample 112 using a heating element that may be integral with sensor 128. An embodiment of the combined biomaterial sample intake port 116 and sampling reservoir 204 is shown in FIG. 7. In FIG. 7 the toilet bowl includes proximity sensor 104 disposed on the side of the bowl connected thereto by a bracing arm. Proximity sensor 104 is disposed toward the front of the toilet bowl as to perceive and notify the other components of the system that person 108 is approaching, in this embodiment. In FIG. 7, sensor 128 is disposed at the back of the toilet bowl and disposed downward toward the water standing in the bowl. The biomaterial sample 112 is deposited into the water and the one or more sensors 128 may analyze the sample therein. Sensor 128 may be configured to detect the timeframe to sample the biomaterial sample 112 as described herein, specifically with reference to FIG. 5. According to embodiments of the disclose subject matter, separate sensors may be utilized to detect the moment sampling should start, the period for which the sampling lasts, when it ends and the measurement of data during that sampling cycle. Additionally or alternatively, biomaterial sample 112 may be transported to one or more enclosed sampling reservoirs 124 disposed in or on the toilet bowl that acts as biomaterial sample intake port 116. Sampling reservoir 124, although shown as interior to the bowl, may be disposed in an internal cavity of the toilet itself, or an additional interior space coupled thereto. The system of FIG. 7 may include an unseen transport assembly 120 that transports biomaterial sample 112 in a gaseous phase to said sampling reservoir 124, and/or the geometry of biomaterial sample intake port 112 may be configured to collect the gaseous phase biomaterial sample 112.

Referring back now to FIG. 1, sensor 128 may be configured to measure one or more parameters related to biomaterial sample 112. The data extraction process may start after biomaterial sample 112 is transferred to one or more sampling reservoirs 124. Sensor 128 or a plurality thereof may perform the data extraction by various sensors and technologies including but not limited to mass spectrometry methods, including such methods of ionization of molecules of organic compounds as electron impact, chemical ionization, pulsed positive negative ion chemical ionization (PPNICI) methods, atmospheric pressure ionization methods, such as electrospray ionization (ESI) or atmospheric pressure chemical ionization (APCI and its subtype—atmospheric pressure photoionization ionization (APPI)) as well as matrix-assisted laser desorption ionization (MALDI). In addition to that data extraction can be processed using sensor-based methods, including but not limited to such sensors as biological, optical, electrochemical, piezoelectric, thermal, metal oxide sensors, gas sensors based on electrically conductive polymers, nanogravimetric biosensors using quartz crystal microbalance (QCM), acoustic sensors, photoionization sensors based on the principle of changing physical (electrical, optical, mechanical, acoustic) or chemical properties when interacting with elements of the environment.

A plurality of sensors 128 or sensory systems can be used either in a static mode when the supply signal does not change over time or in a dynamic mode when the signal changes according to a certain pattern, which makes it possible to increase their specificity and sensitivity, in embodiments. These technologies and methods are used for determining both the biomarkers and the chemical composition of liquids and gases may be known as "Electronic nose", "Electronic tongue", "Artificial nose", "e-nose" and "eNose" to those of ordinary skill in the art.

In some embodiments, the Electronic nose systems (eNose, Artificial Nose systems), and thus sensor 128 can be built using Micro-electromechanical systems (MEMS) Metal-Oxide semiconductor sensors (MOS) such as Mems Nitrogen Dioxide Gas Sensor N02 Gas Detector GM-102b or TC-1326. This sensor consists of sensing material that changes resistance (conductivity) while interacting with some gas molecules, for instance, volatile organic compounds (VOCs from above) and comprise a heating element to provide a certain temperature of mentioned sensing element. The heating element is controlled by a voltage applied to thereto. By applying different voltage different temperature ranges can be achieved as those discussed above. Various temperatures can provide the conditions for sensing elements such as sensor 128 to be sensitive to various chemical components. The heating element may be inside (integrated with) the MOS sensor. The heating element integrated with the MOS sensor is configured to heat sensing elements (semiconductor) to a certain temperature when said sensing element is efficiently interacting with a certain chemical molecule. By varying the temperature modes a single sensor (MOS) may be configured to be sensitive to a broad range of chemical elements (VOCs). According to embodiments of the disclosed subject matter, one of the possible modes at which the MOS sensor is heated to may be 150-550 degrees Celsius. According to embodiments of the disclosed subject matter, one of the possible modes at which the MOS sensor is heated to may be 50-750 degrees Celsius.

The mentioned MOS sensors can be operated in the so-called static mode, when the heating element heats the sensing element of sensor 128 up to a certain temperature which is stable during the measurement process. The MOS sensors can be operated in temperature-modulated mode, when the voltage applied to the heating element is varied and therefore the heating element temperature changes according to some relationship that can be measured and predicted, respectively. Additionally or alternatively, the temperature may be set and conductivity of the MOS is measured consistent with the description of MOS sensors herein.

In embodiments, a single sensor such as sensor 128, or a plurality thereof, can be placed in sampling reservoir 124. Biomaterial sample 112 in gaseous form as described in previous sections can be transferred to the sampling reservoir. A plurality of sensors 128 can work in parallel mode providing separate measurements and information from each of them which can be further compared or combined to obtain higher specificity, sensitivity and accuracy. According to various embodiments, voltages may be applied to sensors including heating elements in steps, periodically or for certain amounts of time. For example and without limitation, in particular, to achieve the objectives of embodiments of the present disclosure, voltage may be applied to the heating element of sensor 128 four times during a measurement cycle: 0.8 volts (V) for 20 seconds (s), 1.2V for 20 s, 2V for 20 s and 2.4V for 20 s. Applying voltage to the heating element provides for reaching temperatures within the range of about 150° C. to 550° C. of the sensing element surface. Voltages may be applied to a plurality of sensors simultaneously at varying levels and for varying amounts of time, in steps, in patterns, or in sequences configured to measure a plurality of chemicals and VOCs. During a measurement cycle, the data extraction systems measure the resistance of the sensor during each voltage (temperature) mode. One of ordinary skill in the art would appreciate these temperature ranges, voltages, and times are merely exemplary embodiments and a plurality of ranges of those inputs can be changed to achieve the intended results. Additionally, embodiments of the present disclosure may inform the temperatures, voltages, times, types of sensors, types of biomaterial samples, and the like.

According to embodiments, sensor 128 may receive other data along with receiving data from MEMS MOS. Additional parameters of biomaterial sample 112 in the sampling reservoir 124 such as pressure, temperature, and humidity to describe biomaterial gas samples can be obtained. For example and without limitation, Adafruit BME280 I2C or SPI Temperature Humidity Pressure Sensor may be utilized to collect these environmental parameters. The measurement cycle can be conducted once for each user's urination or several times per urination or in any other way. In addition to that one probe or sample can be measured (tested) a needed amount of times. After the measurement is conducted the sample transport assembly 120 can release biomaterial sample 112 and clean the chamber as described above. According to embodiments the release of biomaterial sample 112 may be released in different methods. For example and without limitation, liquid biomaterial sample 112 may be flushed down the toilet, pumped through pipes, mains, or the like, or evaporated out of the system. If biomaterial sample 112 is solid, it may be flushed down the toilet, ejected by means of a mechanical actuator like a plunger, trapdoor, blender, crusher, or the like. If biomaterial sample 112 is gaseous, it may be expelled into the atmosphere to dissipate, condensed and ejected in another container, or the like.

According to embodiments of the present disclosure, the information from MEMS MOS, pressure, temperature, and humidity sensors can be saved and processed on the device or transferred to remote computing capacities including cloud computing for advanced feature extraction and person re-identification.

With continued reference to FIG. 1, sensor 128 may be configured to receive a signal from proximity sensor 104 and activate in response to the signal. Sensor 128 may be configured to operate in response to the signal from proximity sensor 104, change modes in response, or a plurality of sensors 128 may be commanded to perform the same or different functions in response to the reception of the signal. Sensor 128 may be configured to determine a timeframe to sample for biomaterial sample 112. For example and without limitation, the signal from proximity sensor 104 may correspond to a person approaching biomaterial sample intake port 116, but sensor 128 may be on a delay such that person 108 may prepare to submit biomaterial sample 112, according to the type of sample such as urine, feces, saliva, breath, or the like. Sensor 128 may be configured to activate after a given amount of time, a pattern of signals, or some other instruction based on information from one or more other sensor. Sensor 128 may include software, hardware or a combination thereof to determine the optimal timeframe to sample for biomaterial sample 112.

For example and without limitation, the device for determining the time of biomaterial sampling can be build using a wide range of sensors including sensor 128, sonars, PIR motion sensor, temperature sensors, pyrometers, light sensors, vibration sensors, time-of-flight (TOF) sensors, weight sensors, sound detection sensors. The sampling time may be an optimal sampling time according to one or more detected physical phenomena. The determination of sampling time may also be launched or operated using manual controllers (buttons, switches, pressure sensors, Bluetooth technology and/or GPS-based sensing technology) or via connected devices such smartphones as described herein. All mentioned physical sensors can be supplied with software placed directly on the device or on other computing solutions (e.g. cloud/remote computation infrastructure) or both.

For example and without limitation, embodiments of the disclosed subject matter may be part of a breath analyzer, a sampling system can use an airflow detection sensor to receive the information that the user has already exhaled and there is enough biomaterial sample 112 in the form of exhaled air that can be transferred and analyzed.

For example and without limitation, embodiments of the disclosed subject matter may be part of a urine volatile organic compound (VOC) analyzer (urine chemical structure, urine chemical composition, urine odor) placed in the restroom, the detection of the right moment of urination can be built using an ultrasound sonar sensor such as HC-SR04 Ultrasonic Sensor Distance Module or time-of-flight sensor such as VL53L0X TIME-OF-FLIGHT DISTANCE SENSOR—30 TO 1000MM GY-530, according to some embodiments. One or more elements of system 100 may indicate that the proper moment for sampling is when there is enough or maximum biomaterial sample in the form of urine in the toilet bowl, which in this case is the biomaterial sample intake port 116 and sampling reservoir 124.

Figure 5:
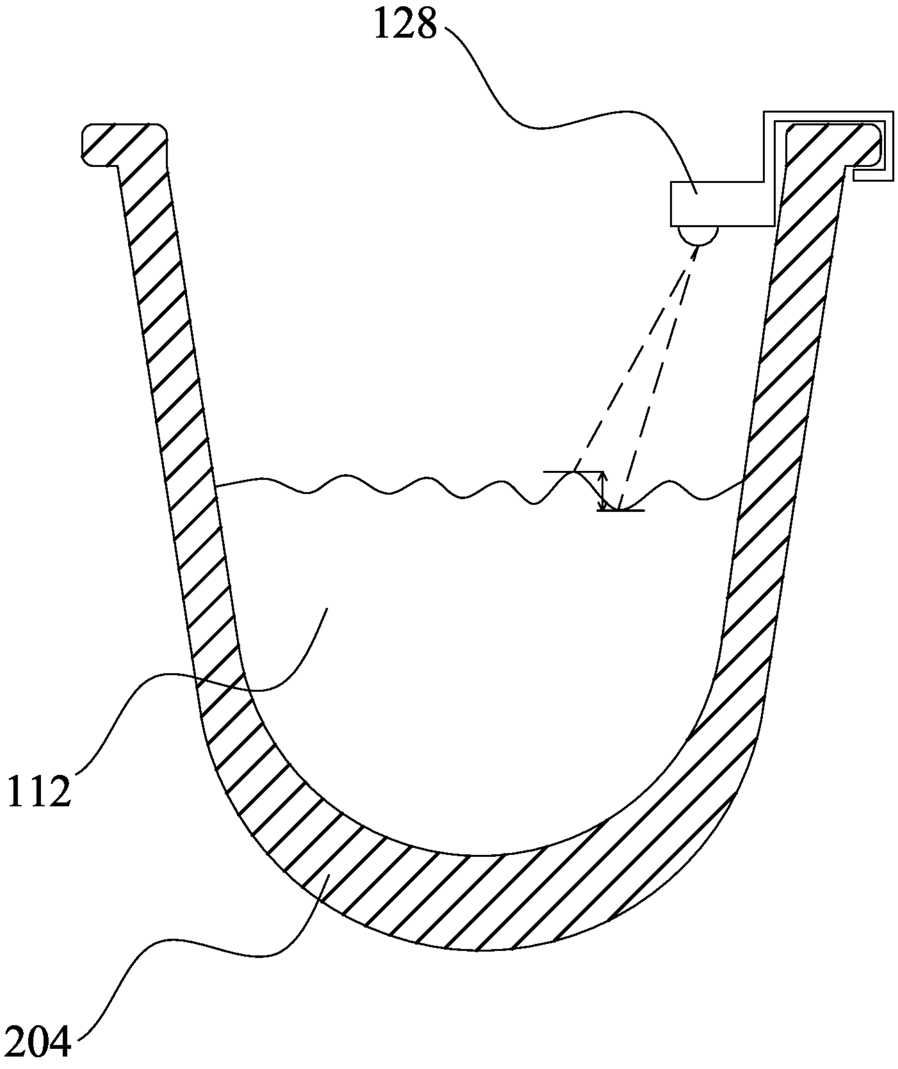
FIG. 5 is a cross-sectional view of a sampling reservoir according to embodiments of the present disclosure.

Referring to FIG. 5, system 100 includes sensor 128 that is configured to detect the timeframe to sample biomaterial sample 112. During the urination process urine stream falls into the water inside the toilet bowl. It generates waves on the surface of the water in the toilet bowl. The decrease in urination leads to a decrease in the intensity of waves inside the toilet bowl and vice-versa. The decrease in waves or their absence can indicate the moment when urination is completed. The detection of waves can be performed with mentioned sensors such as sensor 128 disposed on the side of the toilet bowl as shown, or another sensor or plurality thereof. Using this principle, and with mentioned types of sensors, it is possible to detect the optimal timeframe for sampling. According to embodiments of the disclosed subject matter, the one or more sensors configured to determine the timeframe to sample for biomaterial sample 112 may be separate and standalone to any of the described sensors configured to extract data and may be communicatively coupled thereto. For example and without limitation, sensor 128 as shown in FIG. 5 may include a distinct sensor such as a time-of-flight sensor configured to determine the amplitude of waves in the bowl and communicate to another distinct sensor to measure some parameter of the biomaterial sample 112 there deposited.

Figure 6:
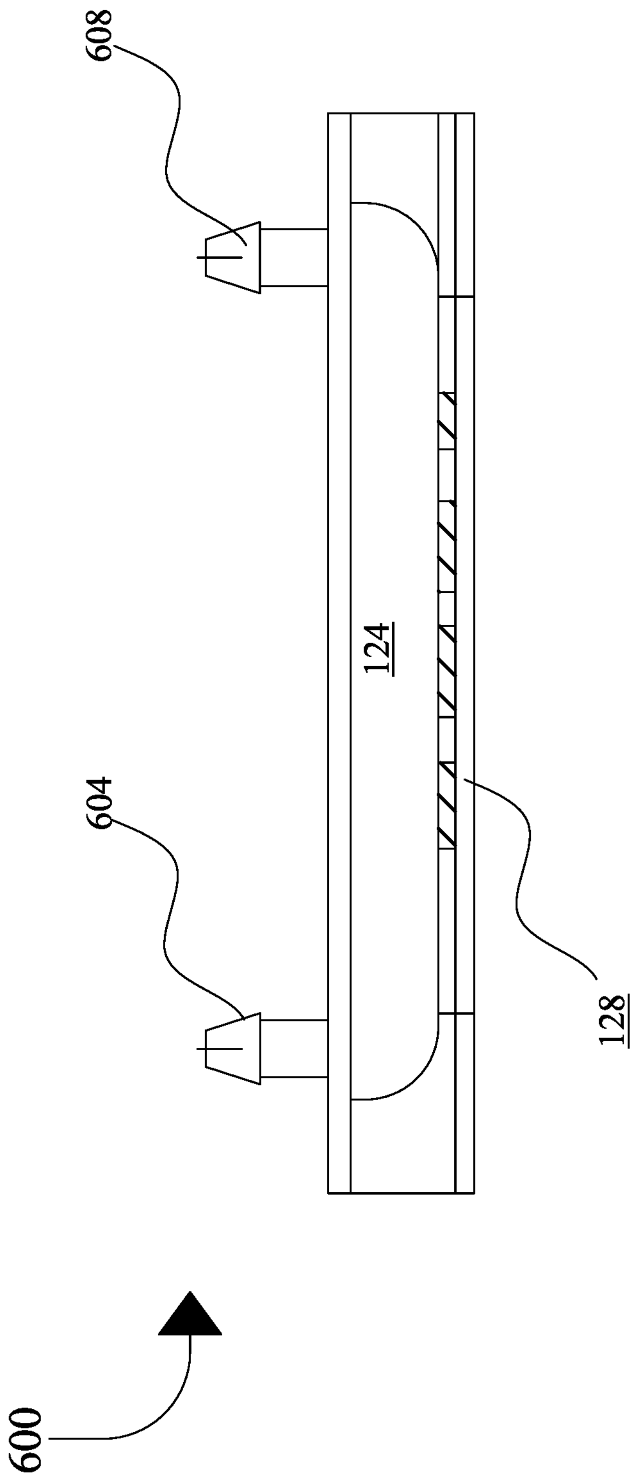
FIG. 6 is a cross-sectional view of a sampling reservoir according to embodiments of the present disclosure.

Referring to FIG. 6, a sampling reservoir 124 is shown in cross-sectional view. Sampling reservoir 124 may be any as described herein. Sampling reservoir 124 may also include an intake nozzle 604 configured to inject gaseous or liquid biomaterial sample 112 into sampling reservoir 124. Intake nozzle 604 may utilize one or more pumps or active methods of transporting fluids based on differing pressure, or may be gravity-assisted, according to embodiments. Sampling reservoir 124 may include exhaust nozzle 608 configured to eject biomaterial sample 112 after measurements have been taken. Exhaust nozzle 608 may utilize any of the methods for ejection of biomaterial sample 112 as described herein. Exhaust nozzle 608 may be mechanically connected to a portion of transport assembly 120 and/or be integral to it. Sampling reservoir 124 includes sensor 128, here shown as part of a sense board configuration wherein one or more sensors 128 are disposed on a printed circuit board, of which at least a portion is exposed to the reservoir. One of ordinary skill in the art would appreciate this embodiment is only exemplary and may be used according to certain biomaterial samples present such as use with an exhaled breath analyzer. This embodiment may be modified to accept a plurality of biomaterial samples 112.

According to embodiments of the disclosed subject matter, the signal from mentioned sensors can be processed using cloud/remote computing or embedded (on device) software. The sampling system such as sensor 128 may be in the form of a standalone device, be integrated with other solutions or devices, or a combination thereof, which will be described in further detail herein.

With continued reference to FIG. 1, system 100 for identification of a person by chemical composition of a biomaterial sample includes sensor 128 configured to extract at least one datum from the biomaterial sample during the optimal timeframe to sample, called extracted data 132. Extracted data 132 may include any measurement discussed herein, alone or in combination. For example and without limitation, extracted data 132 may include chemical composition of VOCs person 108 urine, chemical composition of person 108 exhaled breath, chemical composition of one or more elements found in feces, or the like, according to embodiments of the invention. Extracted data 132 may include temperature, humidity, and/or weight of biomaterial sample 112. Extracted data 132 may include spectrometric data as discussed hereinabove. Extracted data 132 may include information regarding elements, chemicals, alloys, minerals, or the like disposed within biomaterial sample 112. Extracted data 132 may include biological information such as presence of certain bacteria, organisms, cells of a plurality of types and functions, among others. Data extraction of extracted data 132 may be performed in biomaterial sample intake port 116, sampling reservoir 124, transport assembly 120, or any other location, chamber, manifold, or area in which sensor 128 or plurality thereof are disposed.

With continued reference to FIG. 1, system 100 for identification of a person by chemical composition of a biomaterial sample includes a computing node 136. Computing node 136 may be disposed in, on, or nearby to biomaterial sample intake port 116 and/or sampling reservoir 124 in the form of embedded hardware, software, or a combination thereof. Computing node 136 may be in the form of a computer device, minimally equipped with at least one processor device, random access memory and read-only memory as well as data input-output devices. Computing node 136 may include any computer node as described herein.

Computing node 136 is configured to receive at least one datum of extracted data 132 from the biomaterial sample in the form of one or more signals, electrical signals or the like. Computing node 136 may include, but is not limited to one or more devices having hardware and/or software configured for receiving, transmitting and storing data, which can be implemented using both wired and wireless data transmission technologies, including Wi-Fi technology, mobile radio communications using 2G, 3G, 4G, and 5G standards. The configuration of the data transfer device provides for the transfer of data either to one or more local processors, or to one or more cloud systems, or to one or more remote servers. Alternatively, the device for receiving, transmitting and storing data can be designed with the data processing device as a single device or can be integrated with any of the previously listed devices herein.

Computing node 136 includes hardware and/or software configured to extract a first feature 140 from extracted data 132. First feature 140 may be the first of a plurality of extracted features, and in no way limits the number of collection of features intended to be extracted according to embodiments of the disclosed subject matter. First feature 140 may include a feature vector formulated from the extracted data according to the disclosed subject matter or another methodology. First feature may include one or more elements of computer-readable data, human readable data, matrices, listings of numbers, or the like. First feature 140 may include the results of one or more optimization problems, one or more coefficients of one or more polynomials and/or one or more roots of the one or more polynomials according to the disclosed subject matter. First feature 140 may include one or more unique parameters and/or values that describe the composition of a biomaterial sample 112. First feature 140 may include numerical values representing macroscopic parameters corresponding to chemical and/or physical properties of biomaterial sample 112. First feature 140 may be computer interpretable or human interpretable. First feature 140 may include one or more parameters representing a concentration of a chemical compound or group of compounds, in embodiments.

Such a feature extraction device can be integrated into the sampling system or analyzer or be used as an external device connected to the sampling system or to the analyzer by digital data transmission channels. Also, the feature extraction device can be connected by data transmission channels to external data sources or external data processing resources.

Feature extraction can be processed on one or more devices having computing capacities, such as ESP 32 microcontroller, and/or transferred to remote computing capacities.

According to embodiments of the present disclosure, computer node 136 may include a plurality of subsystems, one of which may be a designated feature extraction system. For example and without limitation, the incoming extracted data 136 for the feature extraction system can be a time series of measured values of, for example, conductivity of the sensing element of sensor 128, in particular a plurality of MEMS MOS sensors, under a given change in external influence on the sensitive element of the sensor. Such influences may include, but are not limited, to sensor temperature, sensor voltage or sensor light exposure, among others. External influences are divided into one or more phases in which the dependence of the influencing quantity can be a constant or change according to a given law (e.g., influence modulation).

Computing node 136 then, from the extracted data 132, for each phase, or several phases together, features are extracted, according to the totality of which, for all phases or some of their subsets, a feature vector is built for further use in applications including but not limited to person 108 identification at a later date, disease detection and chemical mixtures classification, among other implementations.

According to embodiments, first feature 140 may be presented in the form of a numerical vector that can be obtained from the input data, by means of transformation such as integral transformation, linear transformation, optimization problem solution, or transformation coefficients of which are determined as a result of the learning process, on a data sample.

In one approach computing node 136 may include a feature extractor that can be implemented as follows:

The initial data for each mixture of substances (biomaterial specimen) is a set $S=(S^1(t), \ldots, S^M(t))$ of M curves $$S^1(t), t\in[0,T_1]; \ldots ; S^M(t), t\in[0,T_M], \qquad \text{Equation 1}$$

each of which describes the changes of the conductivity of the sensor over time, when the sensor is being exposed to this mixture during one of the M phases, where $T_J$—duration of J-th phase. Each phase is characterized by a certain temperature modulation (as described above—influence modulation).

It is assumed that the response $S^J(t), t \in [0, T_J]$ of sensor at time t is a linear combination $$S^J(t) = k_1^J \theta_1^J(t) + \ldots + k_N^J \theta_N^J(t) \quad \text{Equation 2}$$

where N—number of inclusions in the mixture, $$\theta_i^J(t) -$$

fraction of adsorption centers of the sensitive surface of the sensor occupied by molecules of i-th substance at a time t, $$k_{1,\ldots,}^J k_N^J$$

—some positive constants.

The dynamics of filling the sensor surface with mixture substances can be described by differential equations $$d\theta_i^j \frac{(t)}{dt} = \alpha_i^j (1 - \theta^j(t)) - \int \theta_i^j(s) \psi_i^j(t-s) ds \quad \text{Equation 3}$$

with initial condition $$\theta_i^j(0) = c_i^j,\ 0 \le c_i^j < 1,\ \sum c_i^j \le 1.$$

Where $$\theta^J(t) = \theta_1^J(t) + \ldots + \theta_N^J(t)$$

—total fraction of occupied surface adsorption sites at a point in time t, $$\alpha_i^J$$

—concentration coefficients proportional to concentration i-th substances, $$\psi_i^J(t)$$

—a function describing the residence time of an adsorbed molecule i-th substances on the sensor surface before it is desorbed.

As a function $$\psi_i^J(t)$$

you can choose, for example, $$\psi_i^J(t) = \beta_i^J \delta(t),\ \psi_i^J(t) = \beta_i^J e^{-\beta_i^j t},\ \psi_i^J(t) = t^{-\beta_i^J}$$

where $$\beta_i^J$$

—some constant. Note that when $$\psi_i^J(t) = \beta_i^J \delta(t)$$

turns into the classical Langmuir equation for a multicomponent mixture $$d\theta_i^J \frac{(t)}{dt} = \alpha_i^J (1 - \theta^J(t)) - \beta_i^J \theta_i^J(t) \quad \text{Equation 5}$$

Analysis of Equation 3 shows that in the case when $$\psi_i^J(t) = \beta_i^J \delta(t)$$

or when $$\psi_i^J(t) = \beta_i^J e^{-\beta_i^J t},$$

Laplace transform $S^J(\lambda)$ of the sensor response is the ratio of two polynomials $$S^J(\lambda) = A_{2N}^J \frac{(\lambda)}{B_{2N+1}^J}(\lambda) \quad \text{Equation 6}$$

where $$A_{2N}^J(\lambda) = a_0^J \lambda^{2N} + \ldots + a_{2N}^J,\ a_0^J > 0 \quad \text{Equation 7}$$

and $$B_{2N+1}^J(\lambda) = \lambda^{2N+1} + b_1^J \lambda^{2N} + \ldots + b_{2N}^J \lambda,\ b_i^J \ge 0 \quad \text{Equation 8}$$

Equation 6 means that, provided that all the roots of the polynomial $$B_{2N+1}^J(\lambda)$$

are different, the response $S^J(t)$, can be represented as $$S^J(t) = \sum D_k^J \exp\left(\gamma_k^J t\right), \quad \text{Equation 9}$$

where $$\gamma_{1,\ldots,}^J \gamma_{2N+1}^J$$

—polynomial roots $$B^J_{2N+1}(\lambda),$$

a $$D^J_k = A^J_{2N}\frac{(\gamma^J_k)}{(B^J)'_{2N+1}}(\gamma^J_k)$$

Equation 9 can be rewritten as $$S^J(t) = \sum V^J_k \frac{t^k}{k}! \quad \text{Equation 10}$$

$$\text{where } V^J_k = a^J_0 U_{2N+k} + \ldots + a^J_{2N} U_k \quad \text{Equation 11}$$

and $U_k$ are defined recursively $$U_k = 0, k = 0, \ldots, 2N-1 \quad \text{Equation 12}$$

$$U_{2N} = 1 \quad \text{Equation 13}$$

$$U_k = -\sum b^J_i U_{k-i}, k \geq 2N+1 \quad \text{Equation 14}$$

The vector $$f^J = (V^J_{0,\ldots}, V^J_r)$$

of r coefficients $$V^J_{0,\ldots}, V^J_r$$

characterizing the behavior of the first r derivatives of the curve $S^J(t)$ at zero in expansion of Equation 10 is used as a feature vector for training a classifier.

The coefficients of the polynomials $$A^j_{2N}(\lambda), B^j_{2N+1}(\lambda)$$

from Equation 6 also be used as features $f^J=$ $$(a^J_{0,\ldots}, a^J_{2N}, b^J_1, \ldots, b^J_{2N}).$$

Alternatively the set $$\gamma^J_{1,\ldots}, \gamma^J_{2N+1}$$

of polynomial roots of $$B^J_{2N+1}(\lambda)$$

from Equation 9 can be used: $f^J=$ $$(\gamma^J_{1,\ldots}, \gamma^J_{2N+1}).$$

Characteristics vector $f=(f^1, \ldots, f^M) \in R^{Mr}$ can further be used for solving the problem of re-identification, classification of a sick/healthy person, and other tasks of data analysis based on an analysis of the chemical composition.

A weighted classifier can also be built from the classifiers trained separately on individual $f^J$. In particular, if $y^J(x^J(t))$—classifier for phase J of a new observation $x=(x^1(t), \ldots, x^M(t))$, то $y((x^1, \ldots, x^M))=w_1y_1(x^1)+\ldots+w_My_M(x^m)$, where $w_1, \ldots, w_M$—weights, characterizing the quality of classification at each phase, which are determined by the cross-validation procedure.

The values of coefficients of polynomials in (3)

$$A^J_{2N}(\lambda), B^J_{2N+1}(\lambda)$$

are determined by solving the minimization problem $$I^J(N) = |S^J(\lambda)B^J_{2N+1}(\lambda) - A^J_{2N}(\lambda)|^2_2 \rightarrow \min \quad \text{Equation 15}$$

with the limitation $$b^j_i \geq 0, i = 1, \ldots, 2N; a^J_0 > 0.$$

The optimal value N of the number of substances in the mixture is found from the condition $$N^{\hat{}}=\text{argmin}_N \Sigma I^J(N) \quad \text{Equation 16}$$

Polynomial coefficients $$A^J_{2N}(\lambda), B^j_{2N+1}(\lambda)$$

can also be found using the Vector Fitting Algorithm or Steiglitz-McBride Approximation iterative procedure or any other similar solution.

In another approach, computing node 136 may include a feature extractor that solves the optimization problem to fit the measured time series of one or more phases with a predefined function. The determined coefficients of the function or a subset thereof is used as a feature vector of different phases and may be used separately or combined into a joint feature vector.

In another embodiment, computing node 136 may include a feature extractor that uses machine learning to determine the transformation to be applied to input data to produce a feature vector. Either approach may be used alone or in combination.

Processing the information from these sensors is often accompanied by the use of special pattern recognition algorithms, in particular those typical of machine learning ("ML") technologies, which are used to determine the amount and classification of chemicals detected by the above-mentioned sensors. Such algorithms and mathematical models include, without limitation, pattern recognition algorithms, principal component analysis (PCA), linear discriminant analysis (LDA), support vector machines (SVM), artificial neural networks (ANN), and deep learning.

According to embodiments of the invention, adjusting, refining, or tuning of the system can take place according to the following algorithm. When training the system, the user interacts with the system, each time using various technical means, e.g., presses a button and thereby provides the system with information (control signal) affirming or denying that the taken sample is identified with him/her (person 108). Using machine learning technologies (supervised and/or unsupervised), the system is trained to separate the samples collected from different people 108, and after a certain number of cycles the training process ends and the operational stage begins. At this stage, the system itself determines the belonging of a sample to a specific person 108 by comparing the chemical characteristics of the new sample with the information about the chemical characteristics in the one or more databases 148 of the device for receiving, transmitting and storing data (which may be referral values that have been previously established, for example, by machine learning techniques). The formation of a database 148, which contains data on the chemical characteristics of samples of a biomaterial of a particular subject, is carried out by creating an initial record of the chemical characteristics of samples of a subject's biomaterial sample 112. The recording can be performed by pressing a "manual addition of sample" button integrated in a biomaterial sample intake port 116, a sampling system (such as a control signal from system 100), as well as assigning an identifier to the subject of the record. In the further sampling, the correlation of a new sample of biomaterial sample 112 with the data in database 148 is carried out either automatically or in manual mode by again, pressing the "manual addition of sample" button.

With continued reference to FIG. 1, system 100 for identification of a person by chemical composition of a biomaterial sample includes a computing node 136 that may further include an identification module embedded or electrically coupled thereto. The identification module may use the extracted at least a first feature 140 as an input. Identification may use non-learning-based (direct) methods by calculating distances measured from pairs of feature vectors directly or use learning-based methods to further transform the feature vectors before calculating a similarity score. A similarity score can be calculated iteratively between one or more features and/or feature vectors. Computing node 136 may be communicatively coupled to at least one database 148. Database 148 may be one or more electronic storage systems with stored feature 144 retrievably stored therein. Database 148 may be an organized collection of data stored and accessed electronically. According to embodiments, small databases can be stored on a file system, while large databases are hosted on computer clusters or cloud storage, computing node 136 may utilize one or both of these arrangements. The design of database 148 may include formal techniques and practical considerations including data modeling, efficient data representation and storage, query languages, security and privacy of sensitive data, and distributed computing issues including supporting concurrent access and fault tolerance.

Database 148 may include elements of stored feature 144 associated with person 108 based on one or more chemical characteristics of samples previously submitted to the system or transferred electronically from one or more medical data systems. Database 148 may include processed stored feature 144 such as feature vectors associated with the chemical composition of a previously submitted biomaterial sample 112 or other biologically-identifiable data.

Database 148 may include a database management system (DBMS), which is the software that interacts with end users such as computer node 136 and medical personnel or other electronic systems, applications, and the database itself to capture and analyze the data. The DBMS software additionally encompasses the core facilities provided to administer the database. The sum total of the database, the DBMS and the associated applications can be referred to as database 148.

Object identification (ReID) is used in various areas of math and applied solutions in particular the domain of computer vision where visual features are used as a source. In background mathematics, there's no significant difference in what type of feature source is used if feature distributions are compatible with the one or more algorithms employed therein. Consequently, some computer vision-based object identification approaches can be used for person identification based on the chemical structure of biomaterial. Therefore, the proposed system and its method of operation are based on comparing the obtained biomaterial samples 112 of a person 108 with referral data that is stored in the system database (the so-called primary sampling of a subject's biomaterial) and which takes into account the characteristics of the chemical composition of the biomaterial (urine, feces, sweat, saliva, and exhaled air) and the process of automatic identification of a person based on the comparison of the specified data and, as a result, ensuring the complete automation of the medical diagnostics process.

Figure 8:
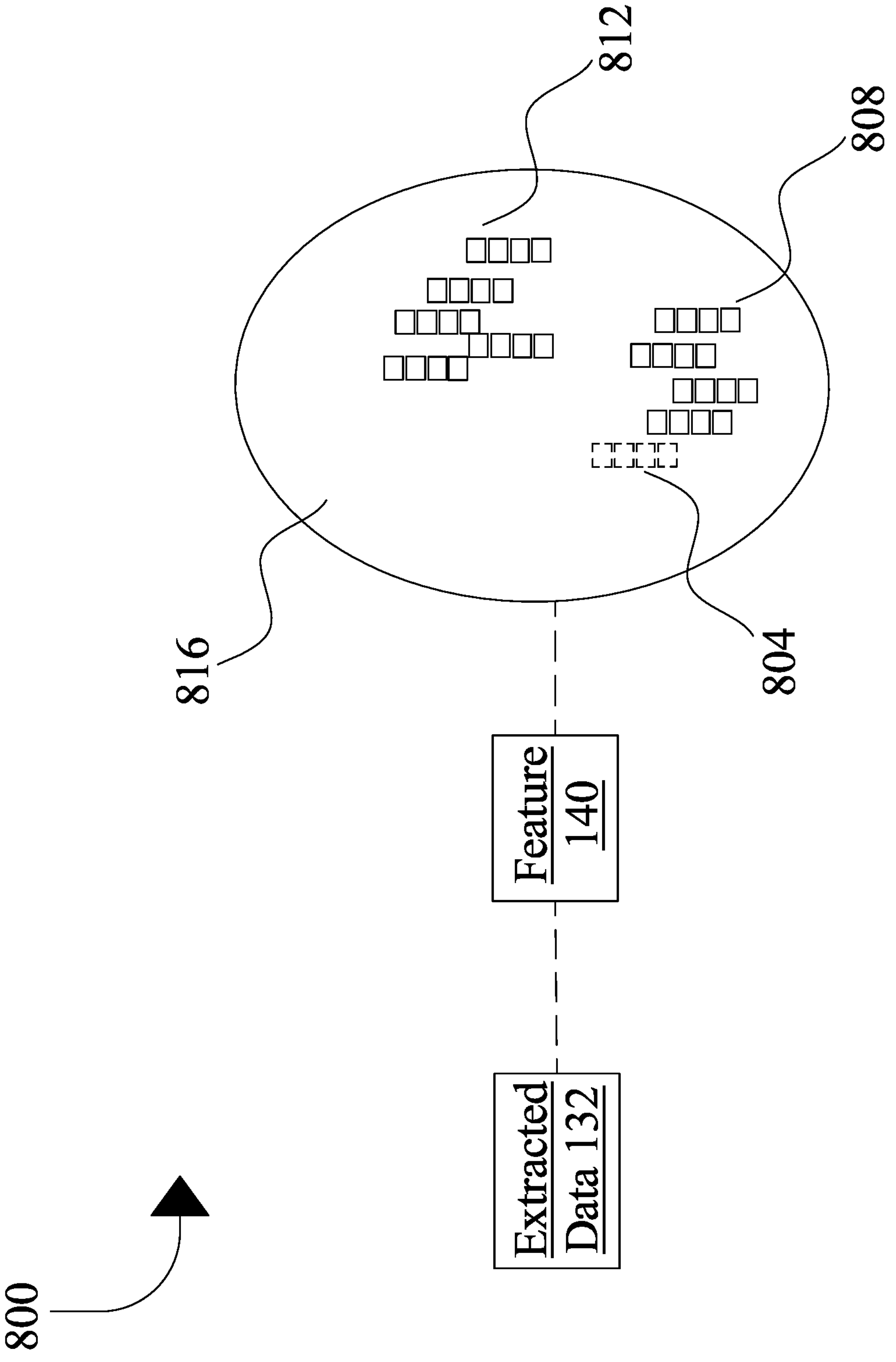
FIG. 8 is a representation of identification of a person by the chemical composition of a biomaterial sample according to embodiments of the present disclosure.

Referring to FIG. 8, identification module 800 may perform person 108 identification problem can be solved by measurements grouping (i.e., clustering) based on feature vectors, where each feature (which may be first feature 140 and/or another parameter) has a direct physical representation. For instance, a first feature 140 can be associated with the concentration of some volatile chemical fractions (biometric markers) of biomaterial sample 112 and be converted into a feature vector 804. An individual person has smaller deviations of parameters within their feature vector in comparison with deviations between measurements for different people. Those features may be stored as stored feature 144 in database 148. One or more algorithms can be used for grouping (clustering) measurements together such as in 808 and 812, in a way that forms a dedicated group (cluster) for each person, in this case two clusters. That is to say, a first feature 140 may be compared to groupings of previously generated features (i.e., stored feature 144), each grouping associated with a person, and the measurement of similarity of the first feature 140 and feature vector 804 to surrounding groupings of features 808 and 812 identifies a person such as person 108 within latent space 816. Any future observation will produce a feature vector within a cluster or close to the cluster so that measurement results can be more likely associated with a correct person, thereby comparing a first feature 140 to stored feature 144. One or more elements of system 100 may utilize one or more ML techniques to improve person 108 over time.

An alternative way is to find similarity in abstract latent space 816 where vectorized representation has no direct physical mapping for each first feature 140 in the vector or their associations are unknown. In this case usage of embedding, vectors can take its place. In data science, these types of vectors are also known as fingerprints.

According to embodiments of the disclosed subject matter, data is processed by comparing the probabilistic distribution of the whole or for a certain zone of first feature 140 of the values of an individual measurement of a biomaterial sample 112 and the probabilistic distribution of these physical quantities on referral data such as stored feature 144, that has been previously obtained, for example, by training the system. Using one or more processors, a similarity score may be calculated between the first and second probability distributions for different zones or for the entire measurement in general. The similarity score can be calculated iteratively using a plurality of algorithms sequentially or by a single process. The process of determining the similarity score can consist of the stages of creating approximating functions and then lowering the dimension of the resulting vector using machine learning algorithms, in embodiments.

The data processing device, using the same processor device or another processor device, also performs identification of a subject by comparing the first probability distribution of a separate measurement of the chemical composition of the biomaterial sample 112, calculated as a referral value, and the second probability distribution of a separate measurement of the chemical composition of the biomaterial sample obtained. The one or more processors perform a similarity determination between the first and the second distribution, e.g., as a function of similarity based on machine-derived weighting factors, whereupon person 108 may be identified.

Data processing can take place in real-time mode or with a time delay between any stages. Alternatively, the identification system can be supplemented with a user interaction system, e.g., in the form of a software application for an external computer device running on the basis of such operating systems as Windows®, MacOS®, iOS®, Android®, etc. Such a user interaction system can receive data from a data processing device and/or an analyzer of chemical characteristics of biomaterial samples or other system data through a device for receiving, transmitting and storing data and can transmit them to a computer device, as well as diagnose or control the identification system through a software application installed on a computer device. Also, the identification system can be supplemented with an integration system with an interface for demonstrating the results of a person's re-identification, which can be designed as specialized medical equipment with a data visualization tool, such as a monitor, a display, and the like.

After the feature extraction phase identification could be processed using such methods as Deep Multi-biometric Fusion for Audio-Visual User identification and Verification, Deep learning-based person identification methods, SphereReID (Deep Hypersphere Manifold Embedding for Person Re-Identification), Deep Cosine Metric Learning for Person Re-Identification, Unsupervised Person identification via Softened Similarity Learning, Person identification with Deep Similarity-Guided Graph Neural Network, Domain adaptation for person identification on new unlabeled data using AlignedReID++, Cross-domain latent space projection for person re-identification, Weakly Supervised Text-based Person Re-Identification.

In some embodiments, the identification function can be made using approaches based on embedding vectors in latent space that makes it possible to detect to which person a measurement belongs to by evaluating cosine or Euclidean distances between those measurements.

Figure 3:
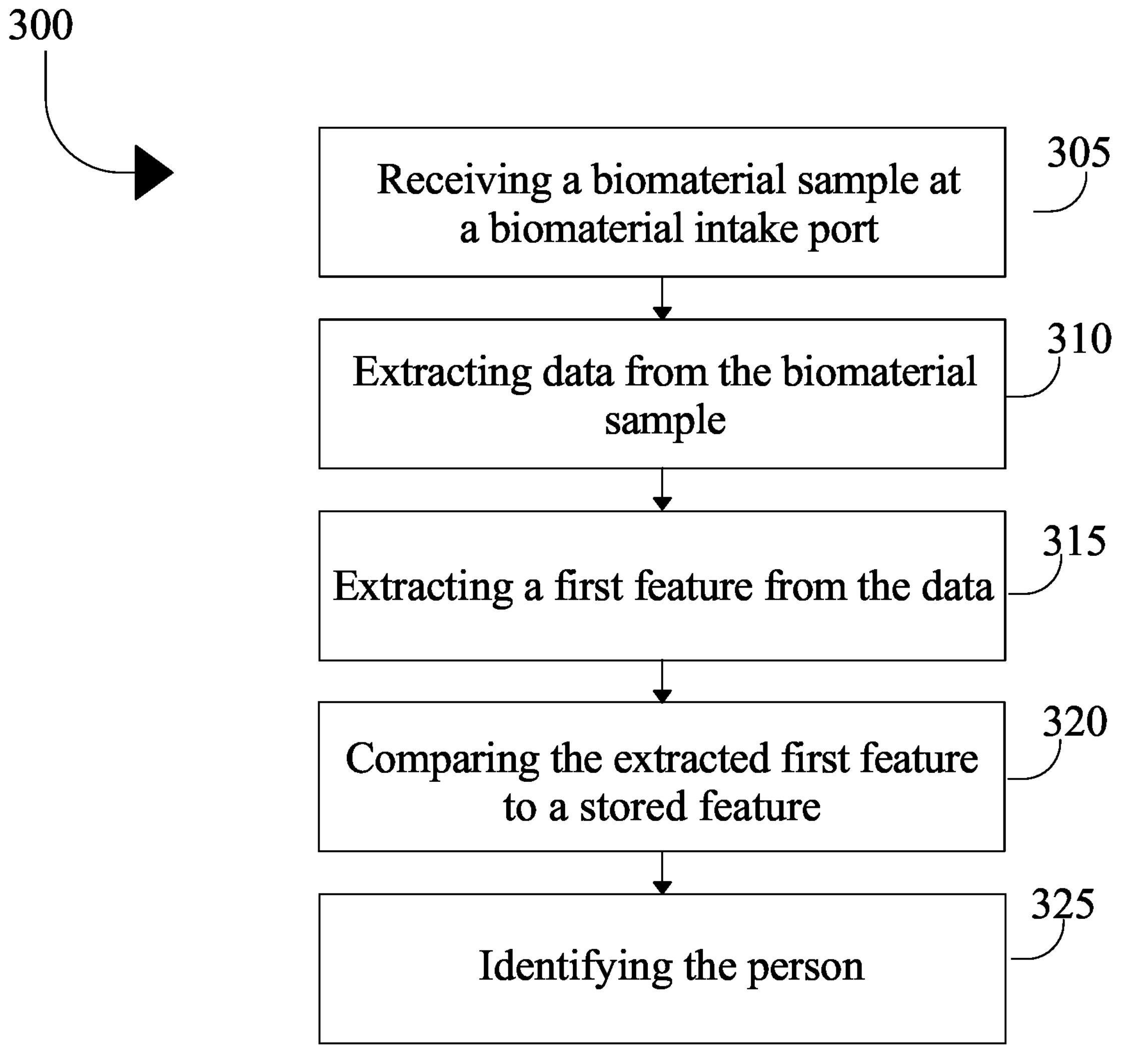
FIG. 3 is a flow diagram representing a method of identification of a person by the chemical composition of a biomaterial sample according to embodiments of the present disclosure.

Referring now to FIG. 3, a method 300 for automated identification of a person by the unique chemical composition of a biomaterial in different phases includes, at step 305, receiving a biomaterial sample 112 at a biomaterial sample intake port 116, wherein receiving the biomaterial sample 112 may include transporting the biomaterial sample 112 to a sampling reservoir 124. The biomaterial sample 112 may be any biomaterial sample 112 as described herein. Biomaterial sample 112 may include urine, feces, sweat, saliva, exhaled air, and/or the gases phases thereof. Biomaterial sample 112 may include volatile organic compounds (VOCs). The biomaterial sample intake port 116 may be any biomaterial sample intake port 116 as described herein. Biomaterial sample intake port 116 may include a breath analyzer, a toilet bowl.

With continued reference to FIG. 3, method 300 for identification of a person by the chemical composition of biomaterial includes, at step 310, extracting data from the biomaterial sample 112, wherein extracting data from the biomaterial sample 112 includes utilizing at least one sensor 128, which may be in the sampling reservoir 124. The biomaterial sample 112 may be any biomaterial sample 112 describe herein. The extracted data 132 may be any extracted data 132 as described herein. The at least one sensor may be any sensor 128 as described herein.

With continued reference to FIG. 3, method 300 for identification of a person by the chemical composition of biomaterial includes, at step 310, includes extracting a first feature 140 from the extracted data 132 representing a chemical composition of the biomaterial sample 112. The first feature may be any first feature 140 as described herein. The extracted data may be any extracted data 132 as describe herein. The biomaterial sample may be any biomaterial sample 112 as describe herein. Extracted data 132 may include information regarding the chemical composition of the biomaterial sample 112. Extracted data 132 may include physical parameters such as temperature, humidity or weight, among others. Extracted data 132 may include mass spectrometric data detailing the elements, molecules, or chemicals present in biomaterial sample 112.

With continued reference to FIG. 3, method 300 for identification of a person by the chemical composition of biomaterial includes, at step 315, includes extracting a first feature from the extracted data. The extracted data 132 may be any extracted data 132 as described herein. The first feature may be any first features 140 as described herein. First feature 140 may include one or more coefficients from one or more polynomials generated by computing node 136, roots of said polynomial, or one or more feature vectors generated from extracted data 132. For example and without limitation, extracted data 132 may include chemical composition of VOCs person 108 urine, chemical composition of person 108 exhaled breath, chemical composition of one or more elements found in feces, or the like, according to embodiments of the invention. Extracted data 132 may include temperature, humidity, and/or weight of biomaterial sample 112. Extracted data 132 may include spectrometric data as discussed hereinabove. Extracted data 132 may include information regarding elements, chemicals, alloys, minerals, or the like disposed within biomaterial sample 112. Extracted data 132 may include biological information such as presence of certain bacteria, organisms, cells of a plurality of types and functions, among others. Data extraction of extracted data 132 may be performed in biomaterial sample intake port 116, sampling reservoir 124, transport assembly 120, or any other location, chamber, manifold, or area in which sensor 128 or plurality thereof are disposed.

With continued reference to FIG. 3, method 300 for identification of a person by the chemical composition of biomaterial includes, at step 320, includes comparing the extracted first feature to a stored feature wherein the stored feature 144 is retrieved from a database 148 and the stored feature 144 comprises identification information associated with person 108. The extracted first feature may be any first feature 140 as described herein. The stored feature 140 may be any stored feature 144 as described herein. Stored features 144 may include identification information of a person such as person 108 in a database 148. The database may be any databased 148 as described herein.

With continued reference to FIG. 3, method 300 for identification of a person by the chemical composition of biomaterial includes, at step 325, includes identifying the person. Identification of person 108 may include an affirmative or negative response such as a "identified" or "not identified" notification to one or more computers, smartphones, screens, audio messages, or text notifications, or the like. Identification of person 108 may include an accuracy or similarity score describing the percentage match of a person 108 to stored data. The person may be any person 108 as describe herein. Person 108 may have stored feature 144 in a database for the comparison as described herein. After the feature extraction phase identification could be processed using such methods as (but not limited to): Deep Multi-biometric Fusion for Audio-Visual User identification and Verification, Deep learning-based person identification methods, SphereReID (Deep Hypersphere Manifold Embedding for Person Re-Identification), Deep Cosine Metric Learning for Person Re-Identification, Unsupervised Person identification via Softened Similarity Learning, Person identification with Deep Similarity-Guided Graph Neural Network, Domain adaptation for person identification on new unlabeled data using AlignedReID++, Cross-domain latent space projection for person re-identification, Weakly Supervised Text-based Person Re-Identification.

The results of identification of person 108 may be applied to local or shared processes via API or other IT systems. For example and without limitation, automated assignment of one or more diagnostic measurements to person 108 may be performed based on the identification. The one or more diagnostic measurements may be specified based on person's 108 medical history and/or analysis of biomaterial sample 112. The automated assignment of further diagnostic measurements may simplify and streamline the process of determining a person's 108 medical needs and current status. Additionally or alternatively, after the identification process is complete, the one or more extracted data, features, medical histories, identification information, and/or health metrics may be transferred to one or more downstream systems. For example and without limitation, these downstream systems may include Medical Information systems, Electronic Health Records, Electronic Medical Records, and the like. Data may be added, subtracted, manipulated, or otherwise communicated based on the identification. Additionally or alternatively, after the identification process the system or one or more connected systems may prompt person 108 to navigate more personal health monitoring systems based on the identification and analysis of biomaterial sample 112. For example and without limitation, after identification of person 108, the system may prompt person 108 to navigate personalized diagnostic plans or administer one or more personalized treatments based on the identification.

Additionally or alternatively the analysis of biomaterial sample 112 may include identifying social health risks such as tuberculosis treatment, air-borne virus, or the like. The system described herein may automatically share health information with one or more social workers, medical professionals and local law enforcement or emergency services, among others. The data extracted and contextual information learned regarding person 108 may be shared with one or more relevant medical providers such as doctors, nurses, specialists, or at home caregivers and support staff thereof.

In some embodiments, the identification function can be made using approaches based on embedding vectors in latent space that makes it possible to detect to which person measurement belongs to by evaluating cosine or Euclidean distances between observations. The chemical structure of biomaterial (e.g. urine) related to one person, distances between corresponding vectors are much smaller than between vectors of different people.

Figure 9:
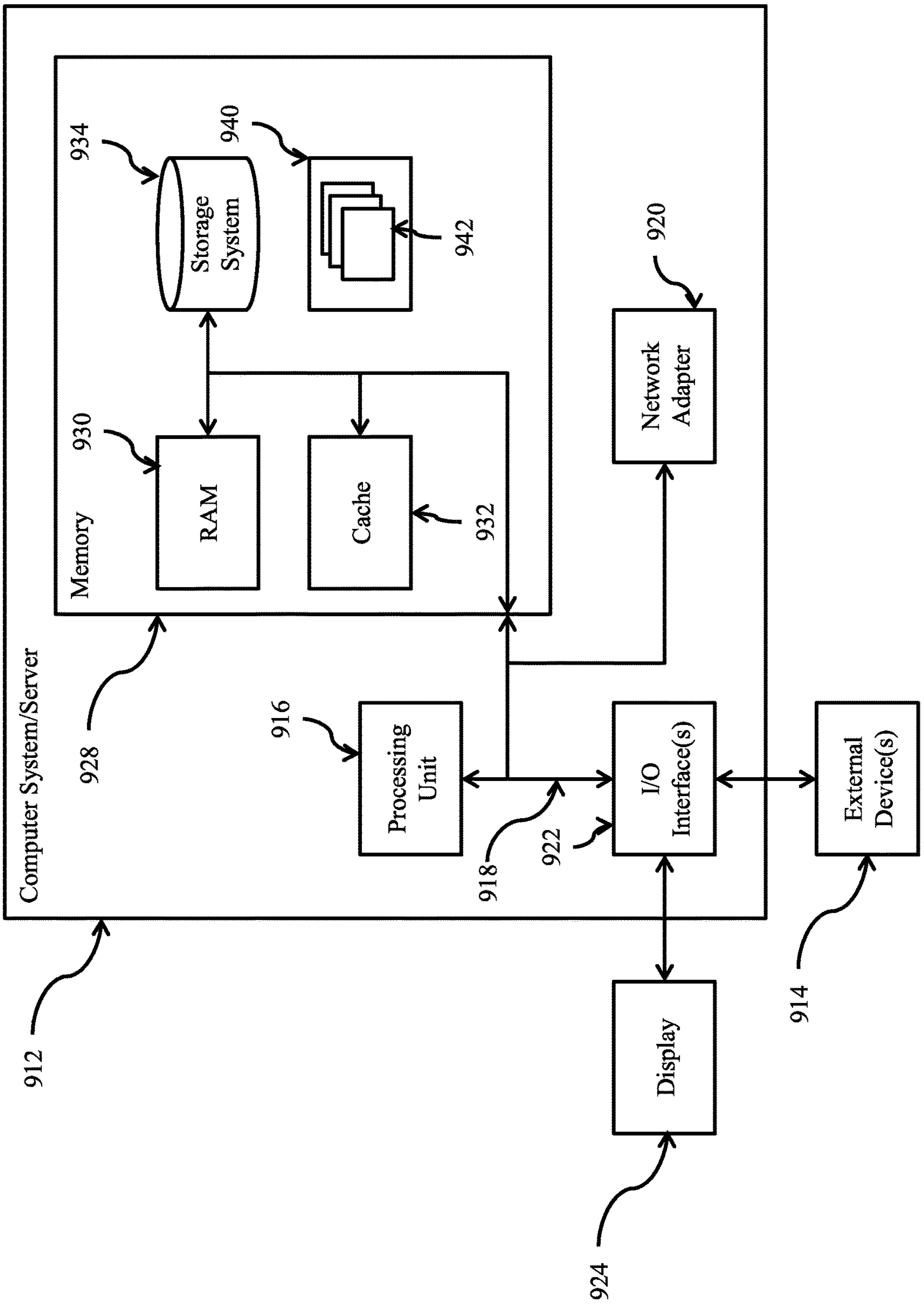
FIG. 9 depicts a computing node according to an embodiment of the present disclosure.

Referring now to FIG. 9, a schematic of an example of a computing node is shown. Computing node 910 is only one example of a suitable computing node and is not intended to suggest any limitation as to the scope of use or functionality of embodiments described herein. Regardless, computing node 910 is capable of being implemented and/or performing any of the functionality set forth hereinabove.

In computing node 910 there is a computer system/server 912, which is operational with numerous other general purpose or special purpose computing system environments or configurations. Examples of well-known computing systems, environments, and/or configurations that may be suitable for use with computer system/server 912 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 912 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 912 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 912 in computing node 910 is shown in the form of a general-purpose computing device. The components of computer system/server 912 may include, but are not limited to, one or more processors or processing units 916, a system memory 928, and a bus 918 that couples various system components including system memory 928 to processor 916.

Bus 918 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 912 typically includes a variety of computer system readable media. Such media may be any available media that is accessible by computer system/server 912, and it includes both volatile and non-volatile media, removable and non-removable media.

System memory 928 can include computer system readable media in the form of volatile memory, such as random access memory (RAM) 930 and/or cache memory 932. Computer system/server 912 may further include other removable/non-removable, volatile/non-volatile computer system storage media. By way of example only, storage system 934 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 918 by one or more data media interfaces. As will be further depicted and described below, memory 928 may include at least one program product having a set (e.g., at least one) of program modules that are configured to carry out the functions of embodiments of the disclosure.

Program/utility 940, having a set (at least one) of program modules 942, may be stored in memory 928 by way of example, and not limitation, as well as an operating system, one or more application programs, other program modules, and program data. Each of the operating system, one or more application programs, other program modules, and program data or some combination thereof, may include an implementation of a networking environment. Program modules 942 generally carry out the functions and/or methodologies of embodiments as described herein.

Computer system/server 912 may also communicate with one or more external devices 914 such as a keyboard, a pointing device, a display 924, etc.; one or more devices that enable a user to interact with computer system/server 912; and/or any devices (e.g., network card, modem, etc.) that enable computer system/server 912 to communicate with one or more other computing devices. Such communication can occur via Input/Output (I/O) interfaces 922. Still yet, computer system/server 912 can communicate with one or more networks such as a local area network (LAN), a general wide area network (WAN), and/or a public network (e.g., the Internet) via network adapter 920. As depicted, network adapter 920 communicates with the other components of computer system/server 912 via bus 918. It should be understood that although not shown, other hardware and/or software components could be used in conjunction with computer system/server 912. Examples, include, but are not limited to microcode, device drivers, redundant processing units, external disk drive arrays, RAID systems, tape drives and data archival storage systems, among others.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A system for automated identification of a person by a unique chemical composition of a biomaterial, the system comprising:
- a biomaterial sample intake port in fluid communication with a sampling reservoir;
- a proximity sensor, the proximity sensor configured to detect a presence of the person at the biomaterial sample intake port and to produce a signal indicative thereof;
- at least one sensor, the at least one sensor in fluid communication with the sampling reservoir and configured to receive the signal from the proximity sensor and in response thereto:
  - prepare a biomaterial sample for analysis by evaporating or sublimating a liquid or a solid biomaterial sample into a gaseous state;
  - determine a timeframe to analyze the biomaterial sample; and
  - extract at least one datum from the biomaterial sample during the timeframe;
- a computing node, the computing node configured to:
  - receive the at least one datum from the sensor;
  - extract a first feature from the at least one datum;
  - compare the first feature to a stored feature associated with the person, thereby identifying the person, wherein said comparing comprises:
    - converting the first feature into one or more first feature vectors; and
    - measuring a distance between the one or more first feature vectors and a cluster of stored feature vectors to determine the similarity between the first feature and the stored feature.

2. The system of claim 1, wherein the biomaterial sample intake port is in fluid communication with the sampling reservoir via a transport assembly.

3. The system of claim 1, wherein the first feature comprises: a feature vector, at least one coefficient of a polynomial, and/or at least one root of the polynomial.

4. The system of claim 1, wherein the proximity sensor comprises: a motion sensor, a sound sensor, a vibration sensor, a SONAR sensor, a time-of-flight sensor, a light sensor, and/or a connected device.

5. The system of claim 4, wherein the connected device comprises a smartphone.

6. The system of claim 1, wherein the sensor is additionally configured to extract the at least one datum from the biomaterial sample in response to manual user input.

7. The system of claim 1, wherein determining the time-frame comprises detecting when there is a predetermined amount of biomaterial sample in the sampling reservoir.

8. The system of claim 1, wherein determining the time-frame comprises determining an amplitude of waves in a fluid disposed in the biomaterial sample intake port.

9. The system of claim 2, wherein the transport assembly comprises a pump.

10. The system of claim 1, wherein the at least one sensor comprises a heating element.

11. The system of claim 10, wherein a voltage is applied to the heating element in increasing steps during a sampling cycle.

12. The system of claim 1, wherein the at least one sensor comprises a mass spectrometer.

13. The system of claim 1, wherein the at least one sensor comprises an electric nose (eNose).

14. The system of claim 1, wherein the biomaterial sample comprises one selected from a group of urine, feces, sweat, saliva, exhaled air, and/or volatile organic compounds (VOC).

* * * * *